United States Patent
Herwig et al.

(10) Patent No.: US 7,084,300 B2
(45) Date of Patent: Aug. 1, 2006

(54) WORK-UP OF RESIDUES IN THE PREPARATION OF CARBOXYLIC ACIDS

(75) Inventors: Juergen Herwig, Huenxe (DE); Ralf Richter, Recklinghausen (DE); Martin Roos, Haltern (DE); Georg Oenbrink, Duelmen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/411,277

(22) Filed: Apr. 11, 2003

(65) Prior Publication Data

US 2003/0195374 A1    Oct. 16, 2003

(30) Foreign Application Priority Data

Apr. 11, 2002  (DE) ............................... 102 15 943

(51) Int. Cl.
*C07C 51/16* (2006.01)
*C07C 51/27* (2006.01)
*C07C 51/42* (2006.01)
*C07C 51/245* (2006.01)

(52) U.S. Cl. .................. 562/524; 562/530; 562/528; 562/540; 562/593

(58) Field of Classification Search ............. 562/593, 562/528, 409, 530, 540, 524
See application file for complete search history.

(56) References Cited

U.S. PATENT DOCUMENTS

| 2,191,786 A | * | 2/1940 | Aronow ...................... 562/540 |
| 2,557,282 A | * | 6/1951 | Hamblet et al. ............ 562/529 |
| 3,112,340 A | * | 11/1963 | Fuchs ......................... 562/528 |
| 3,637,832 A | * | 1/1972 | White et al. ................ 562/530 |
| 3,714,244 A | * | 1/1973 | Okada et al. ............... 562/593 |
| 3,758,564 A | * | 9/1973 | Davis ......................... 562/530 |

FOREIGN PATENT DOCUMENTS

| DE | 16 68 564 | 9/1971 |
| DE | 22 33 590 | 1/1973 |
| FR | 1.331.267 | 8/1962 |
| GB | 1165597 | * 10/1969 |

OTHER PUBLICATIONS

T. P. Hilditch, Catalytic Processes in Applied Chemistry, 1929, D. Van Nostrand Co., xiii-xx.*

* cited by examiner

*Primary Examiner*—Taylor Victor Oh
(74) *Attorney, Agent, or Firm*—Oblon, Spivak, McClelland, Maier & Neustadt, P.C.

(57) ABSTRACT

Degradation acids obtained in the synthesis of carboxylic acids, in particular dicarboxylic acids, having from 8 to 16 carbon atoms may be isolated by separating the degradation acids in the form of a solid from the crude reaction mixture, then washing the degradation acids in the form of an oil with water at an elevated temperature. The resulting degradation acids having low oxidant and metal contents, and the metal catalyst may be recirculated back to the process.

21 Claims, No Drawings

WORK-UP OF RESIDUES IN THE PREPARATION OF CARBOXYLIC ACIDS

BACKGROUND OF THE INVENTION

1. Field of the Invention

The invention relates to a process for working up residues in the preparation of carboxylic acids, in particular the preparation of dicarboxylic acids having from 8 to 16 carbon atoms.

2. Discussion of the Background

The oxidation of, for example, cyclododecanol and cyclododecanone to dodecane-1,12-dioic acid by means of nitric acid in the presence of vanadium catalyst has been described many times in the literature (cf., for example, FR 1331267 and DE 22 33 590). The by-products of this synthesis are mainly dibasic acids having from 4 to 12 carbon atoms, also known as degradation acids, smaller amounts of monobasic acids and nitrogen-containing compounds, and are obtained in one stream after isolation of the main product, dodecanedioic acid. These by-products, which further comprise the vanadium catalyst and other optional metal catalysts such as copper compounds, are formed in small amounts, and can under certain conditions contaminate biological wastewater treatment processes.

The German patent application DE 16 68 564 describes a process in which a by-product stream comprising degradation acids is worked up, and the catalysts, in this case copper and vanadium, are recovered. For this purpose, particular ratios of degradation acids, nitric acid and inorganic salts are set, and the relatively long-chain degradation acids are separated off as an oily phase, while the aqueous nitric acid together with the copper and vanadium catalysts and the short-chain degradation acids are recirculated back into to the process. However, the type of separation method described in DE 16 68 564 is only possible because relatively large amounts of copper salts (>5%) are present in the process and readily phase separate. The is explicitly described in DE 16 68 564. DE 16 68 564 mentions the possibility of simple phase separation by the addition of inorganic sulfates or nitrates of sodium, magnesium or calcium instead of the copper salts. However, if sodium sulfate, for example, is added and is recirculated to the process after phase separation in a manner similar to that described in DE 16 68 564, the crystallization of, for example, the dodecanedioic acid is adversely affected, and is no longer obtained in a form which meets the required specification. In addition, the addition of salts undesirably increases the complexity of the process, because the concentration of these salts also has to be regulated. The type of process described in DE 16 68 564 thus requires the presence of copper salts or other salts which do not adversely affect the crystallization of the desired product.

According to the French patent FR 13 31 267, a small part of the degradation acids, together with nitric acid, catalyst and water may be recirculated directly back to the oxidation process. The remainder is may be passed to a vaporizer in order to recover the nitric acid. This process has the following disadvantages: the relatively long-chain degradation acids which hinder the crystallization are recirculated back to the process, only a small part of the catalyst can be recovered, and the degradation acids cannot be utilized because they are not isolated.

However, it is particularly desirable to isolate the relatively long-chain degradation acids and utilize them directly, for example, or in the form of derivatives, and to recirculate the vanadium catalyst back to the process. In order to utilize the degradation acids, they must contain only small amounts of nitrate (<1%) and metal catalysts (<100 ppm of metal, in particular vanadium), since both components interfere in the further processing of the degradation acids.

It is therefore an object of the invention to provide a process for separating off and isolating the degradation acids formed in the oxidation, which process does not have the abovementioned disadvantages, makes it possible for at least part of the catalyst to be recirculated and provides degradation acids having a quality which makes their further use possible.

SUMMARY OF THE INVENTION

It has now surprisingly been found that isolation of the degradation acids in a satisfactory quality, and recirculation of the catalyst, is possible using a two-stage process in which the degradation acids are first filtered off as a solid, and are then washed at an elevated temperature as an oil.

The present invention accordingly provides a process for working up residues in the preparation of carboxylic acids having from 8 to 16 carbon atoms. In order to isolate the by-products formed in the oxidation (e.g., degradation acids having from 4 to 16 carbon atoms) and to recirculate the catalyst to the oxidation process, a two-stage process is provided in which a portion of the degradation acids is first separated off as a solid by means of a mechanical separation operation, and the separated degradation acids are then washed in the form of an oil at elevated temperature. The degradation acids thus obtained have, in particular, only a small content of an oxidant (anion), for example nitrate, and metal (cation).

DETAILED DESCRIPTION OF THE INVENTION

In contrast to the process of German patent application DE 16 68 564, the degradation acid stream which still contains nitric acid and water but no copper salts and no other inorganic salts may be removed by filtration upon the addition of from 0.5 to 10 parts of water. The amount of water added depends on the composition of the degradation acid stream. The amount of water in the mechanical separation operation is set so that the content of organic acids is from 10 to 50% by weight.

The degradation acids separated off in the mechanical separation step are preferably washed with from 0.5 to 10 parts of water at preferably from 90 to 130° C., particularly preferably from 92 to 98° C.

Any suitable apparatus may be used for the filtration step. For example, a particularly suitable apparatus is a rotary pressure filter; however, the process of the present invention is not restricted to this type of filter. Other possible types of suitable filters are: candle filters, belt filters, drum filters, backwash filters and pressure plate filters. The filtration may be carried out at from 0 to 80° C., preferably from 20 to 40° C. It is very difficult for the degradation acids to be separated off directly as an oil from this stream as taught in DE 16 68 564 because of the low salt concentration and therefore the lack of salting-out effect and the presence of short-chain degradation acids. The short-chain degradation acids act as phase-compatibilizers between the aqueous oxidant, for example the nitric acid, and the relatively long-chain degradation acids and thus prevent the separation of a significant oil phase. The filtrate obtained in this manner contains the major part of the metal, in particular the vanadium, and the nitric acid and is free of relatively long-chain degradation acids which interfere in the crystallization. The filtrate may, if desired after being concentrated, be returned to the oxidation process. The filter residue is preferably washed with water. This washing serves to remove the short-chain degradation acids which can reduce the yield of oil in the subsequent oil washing because of their phase-compatibilizing properties. It is preferred that the filter residue be washed with at least that amount of water which corresponds to the residual moisture content of the filter cake. The residual moisture content is generally 20–80%, based on the total mass of the filter cake. However, the amount of wash water may also be increased to ten times the residual moisture content of the filter cake.

After washing with water, the filter residue may still contain, for example, nitrate and vanadium at a concentration which makes further use difficult or even impossible. In the process of the present invention, this filter residue may be mixed with from 0.5 to 10 parts, preferably from 1 to 5 parts, of water and heated to 80–130° C., preferably 85–100° C., particularly preferably 85–98° C. Heating to relatively high temperatures up to 130° C. is possible in pressure vessels. This procedure results, without the use of copper salts or other salts, in the formation of a two-phase mixture comprising an oil phase and an aqueous phase, since the phase-compatibilizing short-chain degradation acids have been separated off by means of the prior filtration. The aqueous phase contains the major part of the oxidant present in the filter residue, i.e. preferably the nitric acid, the catalyst and small amounts of organic acids. The aqueous phase may be used for diluting the degradation acid stream prior to the filtration. The oil phase comprises the relatively long-chain carboxylic acids and small amounts of catalyst of <100 ppm and small amounts of oxidant (nitric acid) of less than 1%. This oil phase may thus be used further for preparing esters and other chemical compounds.

It is possible to use straight-chain or cyclic hydrocarbons, and in particular the appropriate oxygen-containing compounds such as alcohols or ketones and mixtures thereof as starting materials for the oxidation. For example, suitable starting materials may include cyclododecanol and cyclododecanone and mixtures of cyclododecanol and cyclododecanone.

The oxidant is preferably an inorganic or organic acid having an oxidizing properties, for example nitric acid or a percarboxylic acid such as peracetic acid or a peroxide such as tert-butyl hydroperoxide.

A heavy metal may be present in the oxidation as the catalyst. Examples of suitable metal catalysts may include, in particular, vanadium and copper.

The acid distribution is determined by reacting the acids with diazomethane and analyzing the resulting dimethyl esters by gas chromatography. Vanadium is preferably determined spectroscopically, and nitrate is preferably determined by potentiometric acid-base titration.

Having generally described this invention, a further understanding can be obtained by reference to certain specific examples which are provided herein for purposes of illustration only, and are not intended to be limiting unless otherwise specified.

EXAMPLES

Example 1

100 g of a degradation acid stream having the composition shown below was mixed with 100 g of water at 70° C., cooled to about 20° C. and filtered through a Büchner funnel. 48 g of filter-moist solid and 152 g of filtrate were obtained. The filter residue was mixed with 84 g of water and heated to 94° C. This gave 46.6 g of oil phase and 85.4 g of aqueous phase. The percentages of the degradation acids are based on the organic material which can be eluted in the gas chromatogram.

|  | Degradation acid stream | Filter residue | Filtrate | Oil phase | Aqueous phase |
|---|---|---|---|---|---|
| Mass [g] | 100.0 | 48.0 | 152.0 | 46.6 | 85.4 |
| Nitric acid [%] | 13.1 | 2.6 | 8.2 | 0.5 | n.b. |
| Vanadium content [ppm] | 3800 | 800 | 2300 | 80 | 400 |
| Succinic acid | 9.4 | 1.6 | 15.3 | 0.8 | 10.9 |
| Glutaric acid | 9.5 | 1.6 | 18.6 | 0.9 | 10.0 |
| Adipic acid | 11.5 | 2.5 | 18.0 | 1.5 | 13.6 |
| Pimelic acid | 10.4 | 1.8 | 19.8 | 1.2 | 7.5 |
| Suberic acid | 7.2 | 6.1 | 7.6 | 4.1 | 14.0 |
| Azelaic acid | 3.0 | 1.1 | 6.5 | 0.9 | 1.6 |
| Sebacic acid | 2.5 | 4.0 | 0.6 | 4.0 | 3.3 |
| Undecanedioic acid | 12.9 | 24.5 | 0.1 | 25.6 | 12.0 |
| Dodecanedioic acid | 24.3 | 51.0 | 0.1 | 57.0 | 15.5 |

It is clear from this example that the filtrate contains 80–90% of the nitric acid and the vanadium.

Example 2

900 g of a degradation acid stream having the composition shown below was mixed with 900 g of water at 70° C., cooled to 40° C. and filtered through a Büchner funnel. 714 g of filter-moist solid and 1070 g of filtrate was obtained. 693 g of the filter residue were mixed with 990 g of water and heated to 94° C. This gave 285 g of oil phase and 1377 g of aqueous phase. The percentages of the degradation acids are based on the organic material which can be eluted in the gas chromatogram.

|  | Degradation acid stream | Filter residue | Filtrate | Oil phase | Aqueous phase |
|---|---|---|---|---|---|
| Mass [g] | 900 | 714 | 1070 | 285 | 1.377 |
| Nitric acid [%] | 24 | 10.7 | 13.8 | 0.8 | 4.8 |
| Vanadium content [ppm] | 3800 | 1300 | 1600 | 20 | 680 |
| Succinic acid | 9.4 | 3.71 | 13.2 | 0.52 | 16.6 |
| Glutaric acid | 9.5 | 4.51 | 15.8 | 0.79 | 18.5 |
| Adipic acid | 11.5 | 5.18 | 18.2 | 1.39 | 21.5 |
| Pimelic acid | 10.4 | 5.31 | 17.8 | 2.24 | 17.9 |
| Suberic acid | 7.2 | 3.85 | 11.3 | 2.5 | 9.75 |
| Azelaic acid | 3.0 | 1.98 | 5.77 | 1.68 | 3.43 |
| Sebacic acid | 2.5 | 2.88 | 2.98 | 3.06 | 0.64 |
| Undecanedioic acid | 12.9 | 25.3 | 3.5 | 30.4 | 0.22 |
| Dodecanedioic acid | 24.3 | 40.4 | 0.94 | 52.4 | 0.12 |

Example 3

600 g of a degradation acid stream having the composition shown below were mixed with 1200 g of water at 70° C., cooled to about 20° C. and filtered through a Büchner funnel. 562 g of filter-moist solid and 1192 g of filtrate were obtained. 530 g of the filter residue were mixed with 795 g of water and heated to 94° C. This gave 201 g of oil phase and 1101 g of aqueous phase. The percentages of the degradation acids are based on the organic material which can be eluted in the gas chromatogram.

|  | Degradation acid stream | Filter residue | Filtrate | Oil phase | Aqueous phase |
|---|---|---|---|---|---|
| Mass [g] | 600 | 562 | 1192 | 201 | 1101 |
| Nitric acid [%] | 19.1 | 5.3 | 7.10 | 0.26 | n.b. |
| Vanadium content [ppm] | 3000 | 854 | 1100 | 1.8 | n.b. |
| Succinic acid | 9.4 | 2.98 | 14.31 | 0.42 | 15.49 |
| Glutaric acid | 9.5 | 3.38 | 17.53 | 0.59 | 19.38 |
| Adipic acid | 11.5 | 3.82 | 18.62 | 1.05 | 19.11 |
| Pimelic acid | 10.4 | 3.98 | 19.56 | 1.81 | 18.4 |
| Suberic acid | 7.2 | 3.25 | 10.77 | 2.17 | 9.94 |
| Azelaic acid | 3.0 | 1.83 | 5.84 | 1.79 | 4.12 |
| Sebacic acid | 2.5 | 3.19 | 1.33 | 3.69 | 1.04 |
| Undecanedioic acid | 12.9 | 23.44 | 1.19 | 29.98 | 0.45 |
| Dodecanedioic acid | 24.3 | 42.59 | 0.1 | 53.45 | 0.07 |

Example 4

600 g of a degradation acid stream having the composition shown below were mixed with 600 g of water at 70° C., cooled to about 20° C. and filtered through a Büchner funnel. The filter residue was washed with 700 g of water. 469 g of filter-moist solid and 1400 g of filtrate was obtained. 460 g of the filter residue were mixed with 690 g of water and heated to 94° C. This gave 183 g of oil phase and 965 g of aqueous phase. The percentages of the degradation acids are based on the organic material which can be eluted in the gas chromatogram.

|  | Degradation acid stream | Filter residue | Filtrate | Oil phase | Aqueous phase |
|---|---|---|---|---|---|
| Mass [g] | 600 | 714 | 1070 | 285 | 1377 |
| Nitric acid [%] | 25 | 0.82 | 13.8 | 0.01 | 0.36 |
| Vanadium content [ppm] | 3800 | 100 | 1600 | 15 | 50 |
| Succinic acid | 9.4 | 0.24 | 12.81 | 0.14 | 11.78 |
| Glutaric acid | 9.5 | 0.13 | 15.92 | 0.12 | 12.57 |
| Adipic acid | 11.5 | 0.3 | 18.69 | 0.12 | 17.86 |
| Pimelic acid | 10.4 | 0.19 | 19 | 0.18 | 13.26 |
| Suberic acid | 7.2 | 1.11 | 10.36 | 0.63 | 18.87 |
| Azelaic acid | 3.0 | 0.5 | 5.65 | 0.44 | 5.48 |
| Sebacic acid | 2.5 | 3.73 | 1.84 | 3.07 | 4.42 |
| Undecanedioic acid | 12.9 | 33.59 | 2.44 | 31.73 | 1.58 |
| Dodecanedioic acid | 24.3 | 51.16 | 0.35 | 59.22 | 0.43 |

The priority document of the present application, German application 10215943.2, filed Apr. 11, 2002, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed as new and is intended to be secured by Letters Patent is:

1. A process comprising:
catalytically oxidizing a starting material capable of forming a carboxylic acid by catalytic oxidation, to form a mixture comprising a carboxylic acid having from 8 to 16 carbon atoms and degradation acid by-products having from 4 to 16 carbon atoms;
removing carboxylic acid from the mixture to obtain a degradation acid stream,
separating the degradation acids in the form of a solid from the degradation acid stream;
washing the separated degradation acids with water at an elevated temperature so that the degradation acids are in the form of an oil; and
recovering degradation acid(s).

2. The process of claim 1, further comprising adding from 0.5 to 10 parts of water to the mixture prior to said separating, and said separating is carried out while heating at a temperature of from 80 to 130° C.;
wherein said separating comprises a mechanical separation operation.

3. The process of claim 2, wherein said heating is from 85–100° C.

4. The process of claim 1, wherein an amount of water is present during said separating so that the concentration of organic acids is in the range from 10 to 50% by weight.

5. The process of claim 1, wherein said washing is carried out with from 0.5 to 10 parts of water relative to 100 parts of separated degradation acids at a temperature of from 90 to 130° C.

6. The process of claim 5, wherein said washing is carried out at a temperature of from 92 to 98° C.

7. The process of claim 1, wherein said separating is carried out at a temperature of from 0 to 80° C.

8. The process of claim 1, wherein said separating is carried out at a temperature of from 20 to 40° C.

9. The process of claim 1, wherein said separating is carried out using a rotary pressure filter or a backwash filter.

10. The process of claim 1, wherein said catalytic oxidation is carried out in the presence of an oxidizing acid.

11. The process of claim 10, wherein the oxidizing acid is nitric acid.

12. The process of claim 1, wherein said starting material comprises cyclododecanol or cyclododecanone, or a mixture thereof.

13. The process of claim 1, wherein said catalytically oxidizing is carried out in the presence of vanadium.

14. A process, comprising:
catalytically oxidizing a starting material capable of forming a carboxylic acid by catalytic oxidation, to form a mixture comprising a carboxylic acid having from 8 to 16 carbon atoms and degradation acid by-products having from 4 to 16 carbon atoms,
removing carboxylic acid from the mixture to obtain a degradation acid stream,
separating the degradation acids in the form of a solid from the degradation acid stream,
washing the separated degradation acids with water at an elevated temperature so that the degradation acids are in the form of an oil, and
recovering degradation acid(s), and
recirculating catalyst removed from the degradation acids back to the oxidation process.

15. A process for working up residues in the preparation of carboxylic acids having from 8 to 16 carbon atoms, wherein, to isolate the by-products formed in the oxidation (degradation acids having from 4 to 16 carbon atoms) and to optionally recirculate the catalyst to the oxidation process, a two-stage process in which part of the degradation acids is first separated off as a solid by means of a mechanical separation operation and is then washed as an oil at elevated temperature is carried out.

16. The process according to claim 1, which proceeds without the use of copper salts.

17. The process according to claim 2, wherein no copper salt is added to the mixture prior to said separating.

18. The process according to claim 14, which proceeds without the use of copper salts.

19. The process according to claim 15, which proceeds without the use of copper salts.

20. The process according to claim 1, wherein said degradation stream contains no copper salts and no other inorganic salts.

21. A process comprising:
   catalytically oxidizing a starting material selected from the group consisting of straight-chain alcohols, cyclic alcohols, straight-chain ketones, cyclic ketones and mixtures thereof, to form a mixture comprising a carboxylic acid having from 8 to 16 carbon atoms and degradation acid by-products having from 4 to 16 carbon atoms;

removing carboxylic acid from the mixture to obtain a degradation acid stream, separating the degradation acids in the form of a solid from the degradation acid stream;

washing the separated degradation acids with water at an elevated temperature so that the degradation acids are in the form of an oil; and recovering degradation acid(s).

* * * * *